(12) United States Patent
Ivachtchenko et al.

(10) Patent No.: US 9,085,539 B2
(45) Date of Patent: *Jul. 21, 2015

(54) CYCLIC N,N'-DIARYLTHIOUREA—ANDROGEN RECEPTOR ANTAGONIST, ANTI BREAST CANCER COMPOSITION AND USE THEREOF

(71) Applicants: Alexandre Vasilievich Ivachtchenko, Encinitas, CA (US); Oleg Dmitrievich Mitkin, Moscow reg. (RU)

(72) Inventors: Alexandre Vasilievich Ivachtchenko, Encinitas, CA (US); Oleg Dmitrievich Mitkin, Moscow reg. (RU)

(*) Notice: Subject to any disclaimer, the term of this patent is extended or adjusted under 35 U.S.C. 154(b) by 4 days.

This patent is subject to a terminal disclaimer.

(21) Appl. No.: 13/831,929

(22) Filed: Mar. 15, 2013

(65) Prior Publication Data

US 2013/0252992 A1    Sep. 26, 2013

Related U.S. Application Data

(63) Continuation-in-part of application No. 13/811,282, filed as application No. PCT/RU2011/000476 on Jul. 1, 2011.

(30) Foreign Application Priority Data

Jul. 22, 2010 (RU) .................... 2010130618

(51) Int. Cl.
| | |
|---|---|
| *A61K 31/505* | (2006.01) |
| *C07D 233/86* | (2006.01) |
| *C07D 491/107* | (2006.01) |
| *C07D 471/10* | (2006.01) |

(52) U.S. Cl.
CPC ............ *C07D 233/86* (2013.01); *C07D 471/10* (2013.01); *C07D 491/107* (2013.01)

(58) Field of Classification Search
None
See application file for complete search history.

*Primary Examiner* — Craig Ricci

(57) ABSTRACT

The present invention relates to novel cyclic N,N'-diarylurea—androgen receptor antagonist, anti-cancer agent, pharmaceutical composition, medicament, and method for treatment of breast cancer disease.

Figure 1:
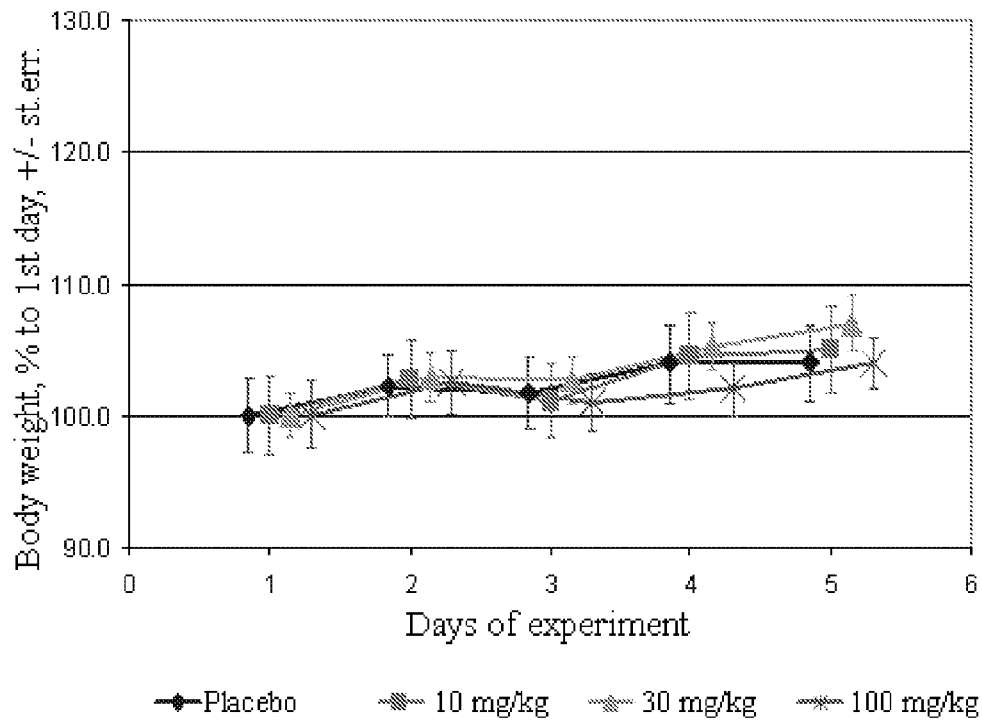

Cyclic N,N'-diarylthioureas or N,N'-diarylureas of the general formula 1, their optical (R)- and (S)-isomers and pharmaceutically acceptable salts thereof exhibiting properties of androgen receptor antagonists have been proposed, 1.2

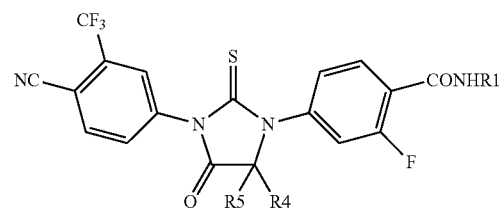

wherein:
R1 represents $C_1$-$C_3$ alkyl;
R4 and R5 represent hydrogen; or
R4 represents hydrogen, R5 represents methyl; or
R4 represents methyl, R5 represents $CH_2R6$ group in which R6 is $C_1$-$C_3$ alkoxycarbonyl, carboxyl, hydroxyl group optionally substituted with methyl or benzyl; or
R4 and R5 together with the carbon atom they are attached to form 5- or 6-membered saturated heterocycle including at least one oxygen atom or nitrogen atom optionally substituted with methyl.

5 Claims, 2 Drawing Sheets

*-p<0.05 in comparison with placebo group (ANOVA)

CYCLIC N,N'-DIARYLTHIOUREA—ANDROGEN RECEPTOR ANTAGONIST, ANTI BREAST CANCER COMPOSITION AND USE THEREOF

CROSS REFERENCE TO RELATED APPLICATIONS

This application is a continuation-in-part of U.S. application Ser. No. 13/811,282 filed Jan. 21, 2013, which claims benefit of priority to the International application PCT/RU2011/000476 filed Jul. 1, 2011, which claims benefit of foreign priority to the Russian Federation application RU 2010130618 of Jul. 22, 2010. The priority applications are hereby incorporated by reference in their entirety.

FIELD OF THE INVENTION

The invention relates to novel cyclic N,N'-diarylthioureas and N,N'-diarylureas—androgen receptor antagonists, anticancer agent, pharmaceutical composition, medicament and method for treatment of cancer including prostate cancer.

PRIOR ART

There are known androgen receptor antagonists which are -1,3-diaryl-5,5-dimethyl-2-thioxoimidazolidin-4-ones I, 5,7-diaryl-6-thioxo-5,7-diazaspiro[3,4]octan-8-ones II and 1,3-diaryl-2-thioxo-1,3-diazaspiro[4,4]nonan-4-ones III exhibiting anticancer activity [WO2006124118, WO2007127010]. Amongst these compounds the most promoted is 4-[3-[4-cyano-3-(trifluoromethyl)phenyl]-5,5-dimethyl-4-oxo-2-thioxoimidazolidin-1-yl]-2-fluoro-N-methylbenzamide MDV3100 (androgen receptor antagonist with $IC_{50}$=36 nM), which is now in the III phase of clinical trials as medicament for prostate cancer treatment [*Drug Data Rep.*, 2009, 31(6), 609].

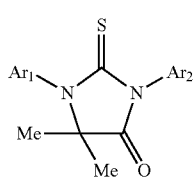

I

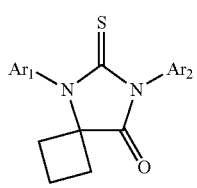

II

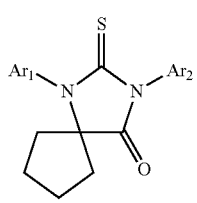

III

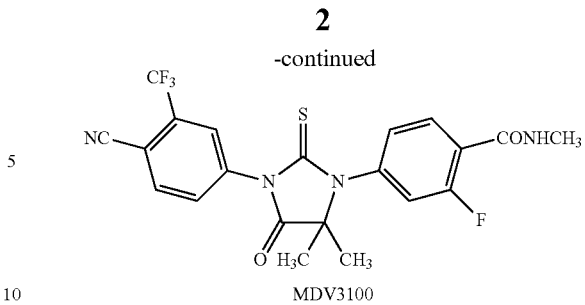

MDV3100

Searching for highly effective anticancer medicaments exhibiting enhanced activity and reduced toxicity, is still one of the main directions in the development of novel pharmacological remedies for cancer treatment, including prostate cancer. In this context the development of novel anticancer active agents, pharmaceutical compositions and medicaments, and also methods for their preparation and use is of essential importance.

DISCLOSURE OF THE INVENTION

In the context of the invention, the terms are generally defined as follows:

"Azaheterocycle" means an aromatic or non aromatic mono- or poly-cyclic system, comprising at least one nitrogen atom in the cycle. Azaheterocycle may have one or more "cyclic system" substituents.

"Active component" (drug-substance) means a physiologically active compound of synthetic or other origin (biotechnological, vegetable, animal, microbe and so on), exhibiting pharmacological activity and being an active component of pharmaceutical composition, employing in production and preparation of medicaments.

"Alkyl" means an aliphatic hydrocarbon straight or branched chain with 1-12 carbon atoms. Branched means an alkyl chain with one or more "lower alkyl" substituents. Alkyl group may have one or more substituents of the same or different structure ("alkyl substituent") including halogen, alkenyloxy, cycloalkyl, aryl, heteroaryl, heterocyclyl, aroyl, cyano, hydroxy, alkoxy, carboxy, alkynyloxy, aralkoxy, aryloxy, aryloxycarbonyl, alkylthio, heteroarylthio, aralkylthio, arylsulfonyl, alkylsulfonylheteroaralkyloxy and so on.

"Antagonists" mean ligands which being bound to definite receptors not cause active cellular responses. Antagonists prevent linkage between agonists and receptors and by that block specific receptor signal transmission.

"Aryl" means aromatic mono- or poly-cyclic system with 6-14 carbon atoms, predominantly 6-10 carbon atoms. Aryl may have one or more "cyclic system substituents" of the same or different structure. Phenyl, substituted phenyl, naphthyl, or substituted naphthyl are the representatives of aryl groups. Aryl could be annelated with nonaromatic cyclic system or heterocycle.

"Heterocyclyl" means aromatic or saturated mono- or polycyclic system with 3-10 carbon atoms, preferably from 5 to 6, wherein one or more carbon atoms are substituted by one or more heteroatoms, such as N, S or O. Prefix "aza", "oxa" or "thia" before "heterocyclyl" means that N, O or S atoms are introduced in the cycle, respectively. Heterocyclyl may have one or more "cyclic system substituents" of the same or different structure. N- and S-atoms of heterocyclyl cycle could be oxidized to N-oxide, S-oxide or S-dioxide. Piperidinyl, pyrrolidinyl, piperazinyl, morpholinyl, thiomorpholinyl, thiazolidinyl, 1,4-dioxane-2-yl, tetrahydrofuranyl, tetrahydrothiophenyl and others are examples of heterocyclyl.

"Hydrate" means stoichiometric or nonstoichiometric compositions of compounds or their salts with water.

"Substituent" means a chemical radical attached to scaffold (fragment), for example, "alkyl substituent", "amino group substituent", "carbamoyl substituent", and "cyclic system substituent", the meanings of which are defined in this section.

"Medicament"—is a compound (or mixture of compounds in the form of pharmaceutical composition) in the form of tablets, capsules, injections, ointments and other ready forms intended for restoration, improvement or modification of physiological functions at humans and animals, and also for treatment and prophylaxis of diseases, diagnostics, anesthesia, contraception, cosmetology and others.

"Lower alkyl" means a straight or branched alkyl with 1-4 carbon atoms.

"Pharmaceutical composition" means a composition comprising a compound of general formula 1 or 1.2 and at least one of components selected from the group consisting of pharmaceutically acceptable and pharmacologicaly compatible fillers, solvents, diluents, auxiliary, distributing and sensing agents, delivery agents, such as preservatives, stabilizers, disintegrators, moisteners, emulsifiers, suspending agents, thickeners, sweeteners, flavouring agents, aromatizing agents, antibacterial agents, fungicides, lubricants, and prolonged delivery controllers, the choice and suitable proportions of which depend on the nature and way of administration and dosage. Examples of suitable suspending agents are ethoxylated isostearyl alcohol, polyoxyethene, sorbitol and sorbitol ether, microcrystalline cellulose, aluminum metahydroxide, bentonite, agar-agar and tragacant and their mixtures as well. Protection against the action of microorganisms can be provided by various antibacterial and antifungal agents, such as, for example, parabens, chlorobutanole, sorbic acid, and similar compounds. Composition may also contain isotonic agents, such as, for example, sugar, sodium chloride, and similar compounds. Prolonged effect of composition may be achieved by agents slowing down absorption of active ingredient, for example, aluminum monostearate and gelatine. Examples of suitable carriers, solvents, diluents and delivery agents include water, ethanol, polyalcohols and their mixtures, natural oils (such as olive oil) and organic esters (such as ethyl oleate) for injections. Examples of fillers are lactose, milk-sugar, sodium citrate, calcium carbonate, calcium phosphate and the like. Examples of disintegrators and distributors are starch, alginic acid and its salts, and silicates. Examples of suitable lubricants are magnesium stearate, sodium lauryl sulfate, talc and polyethylene glycol of high molecular weight. Pharmaceutical composition for peroral, sublingval, transdermal, intramuscular, intravenous, subcutaneous, local or rectal administration of active ingredient, alone or in combination with another active compound may be administered to humans and animals in standard administration form, or in mixture with traditional pharmaceutical carriers. Suitable standard administration forms include peroral forms such as tablets, gelatin capsules, pills, powders, granules, chewing-gums and peroral solutions or suspensions, sublingval and transbuccal administration forms; aerosols; implants; local, transdermal, subcutaneous, intramuscular, intravenous, intranasal or intraocular forms of introduction and rectal administration forms. Pharmaceutical compositions are usually prepared by means of standard procedures by mixing an active compound with liquid or over-grounded solid carrier.

"Pharmaceutically acceptable salt" means a relatively non-toxic both organic and inorganic salts of acids and bases disclosed in this invention. Salts could be prepared in situ in processes of synthesis, isolation or purification of compounds or be prepared specially. In particular, bases salts could be prepared starting from purified base of disclosed compound and suitable organic or mineral acid. Examples of salts prepared in this manner include hydrochlorides, hydrobromides, sulfates, bisulfates, phosphates, nitrates, acetates, oxalates, valeriates, oleates, palmitates, stearates, laurates, borates, benzoates, lactates, p-toluenesulfonates, citrates, maleates, fumarates, succinates, tartrates, methane sulphonates, malonates, salicylates, propionates, ethane sulphonates, benzene sulfonates, sulfamates and the like (Detailed description of properties of such salts is given in: Berge S. M., et al., "Pharmaceutical Salts" J. Pharm. Sci., 1977, 66: 1-19). Salts of disclosed acids may be also prepared by reaction of purified acids specifically with suitable base; moreover, metal salts and amine salts may be synthesized too. Metal salts are salts of sodium, potassium, calcium, barium, magnesium, zink, lithium and aluminum, sodium and potassium salts being preferred. Suitable inorganic bases from which metal salts can be prepared are sodium hydroxide, carbonate, bicarbonate and hydride; potassium hydroxide, carbonate and bicarbonate, lithium hydroxide, calcium hydroxide, magnesium hydroxide, zinc hydroxide. Organic bases suitable for preparation of disclosed acid salts are amines and amino acids of sufficient basicity to produce stable salt suitable for medical purposes use (in particular, they are to have low toxicity). Such amines include ammonia, methylamine, dimethylamine, trimethylamine, ethylamine, diethylamine, triethylamine, benzylamine, dibenzylamine, dicyclohexylamine, piperazine, ethylpiperidine, tris(hydroxymethyl)aminomethane and the like. Besides, salts can be prepared using some tetraalkylammonium hydroxides, such as holine, tetramethylammonium, tetraethylammonium, and the like. Aminoacids may be selected among main aminoacids-lysine, ornithine and agrinine.

The authors have disclosed novel cyclic N,N'-diarylthioureas and N,N'-diarylureas of the general formula 1, an optical (R)- or (S)-isomer, or a pharmaceutically acceptable salts thereof, which are androgen receptor antagonists:

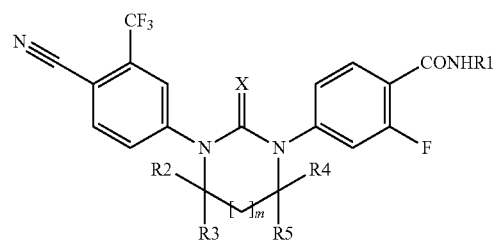

wherein:
X represents oxygen or sulfur;
m=0 or 1;
R1 represents $C_1$-$C_3$alkyl;
R2 and R3 represent hydrogen; or
R2 and R3 together with the C-atom they are attached to form C=O group;
R4 and R5 represent hydrogen; or
R4 represents hydrogen, R5 represents methyl; or
R4 represents methyl, R5 represents $CH_2$R6 group in which R6 is $C_1$-$C_3$ alkoxycarbonyl; carboxyl; hydroxyl group optionally substituted with methyl or benzyl; or
R5 and R4 together with the C-atom they are attached to form 5- or 6-membered heterocycle comprising at least one oxygen atom or nitrogen atom optionally substituted with methyl; or R4 and R5 together with the C-atom they are attached to represent NH group.

The preferred compounds are N,N'-diarylthioureas and N,N'-diarylureas, their optical (R)- and (S)-isomers and pharmaceutically acceptable salts of the general formulas 1.2, 1.3 or 1.4:

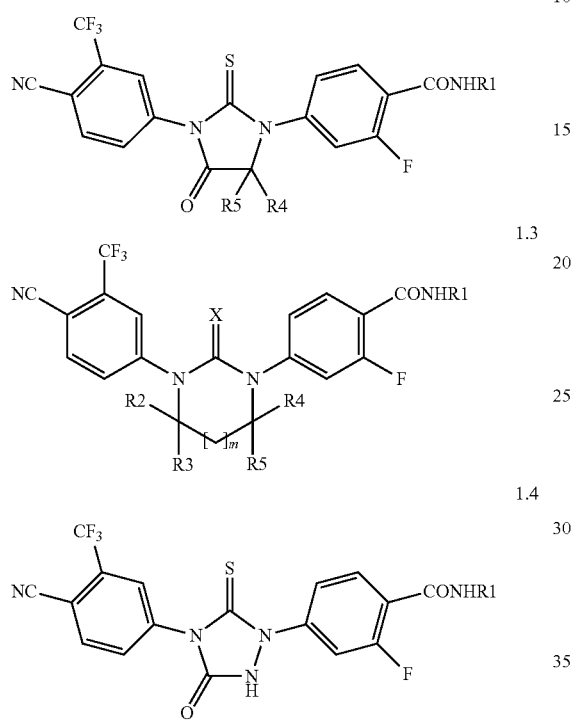

wherein:
X, R1, R2, R3, R4 and R5 have the above meanings

The more preferable compounds are cyclic N,N'-diarylthioureas of formulas 1.2(1), 1.2 (2), 1.2.2 and 1.2.3, their optical (R)-isomers—(R)-1.2(2), (R)-1.2.2, (R)-1.2.3 and (S)-isomers—(S)-1.2(2), (S)-1.2.2 and (S)-1.2.3:

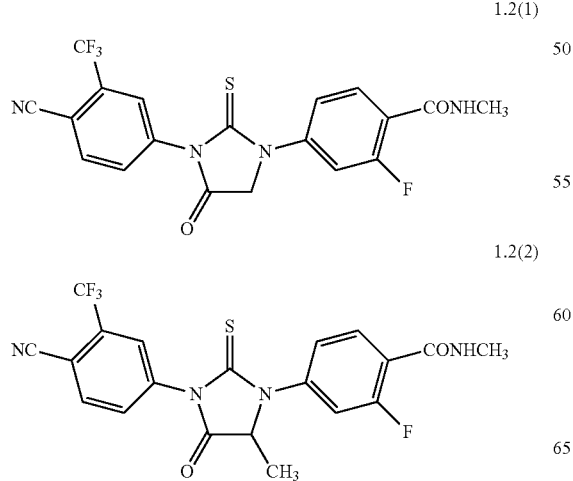

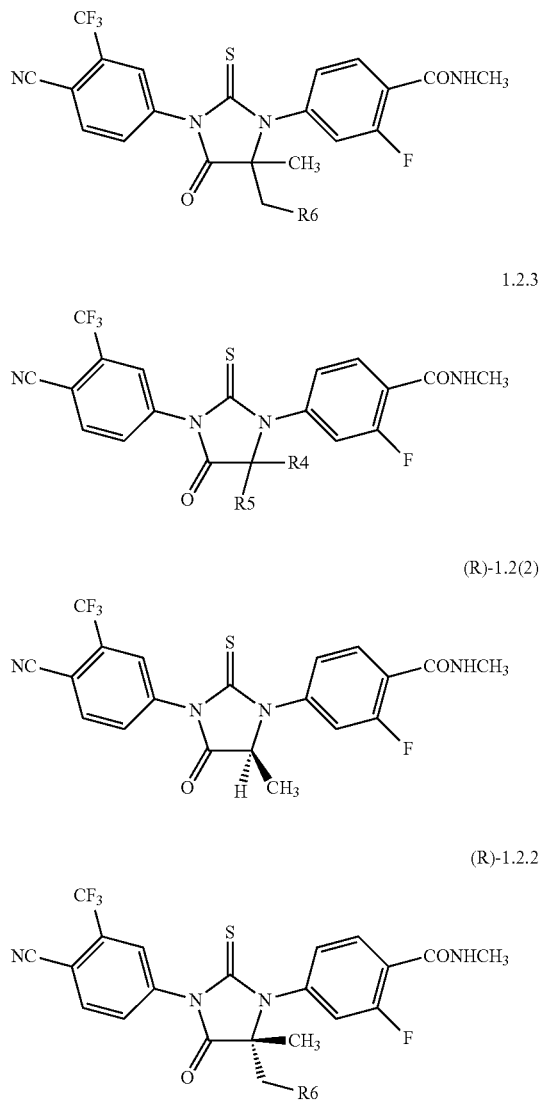

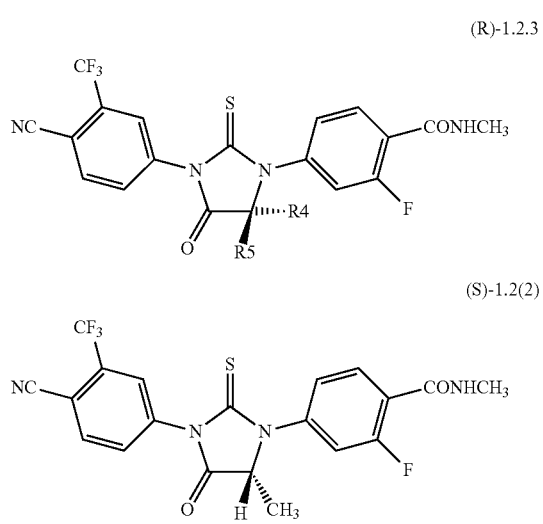

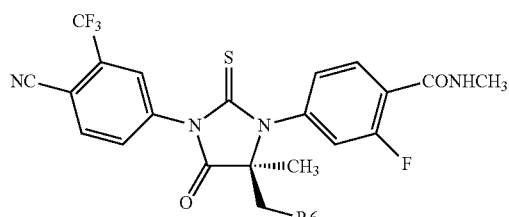

(S)-1.2.2

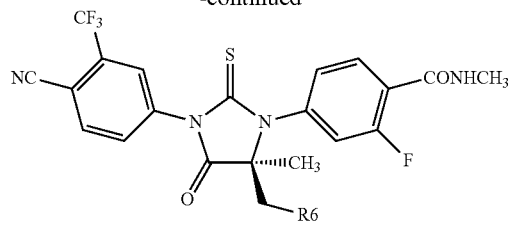

(S)-1.2.2(1): R6 = OCH₃;
(S)-1.2.2(2): R6 = OCH₂Ph;
(S)-1.2.2(3): R6 = OH;

(S)-1.2.3

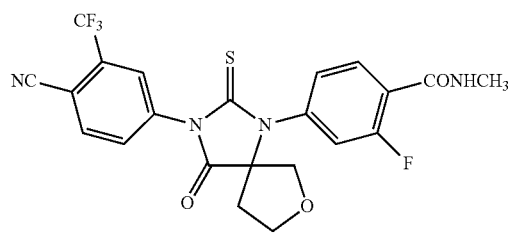

1.2.3(1)

wherein:

R5 and R4 together with the C-atom they are attached to form 5- or 6-membered heterocycle comprising at least one oxygen atom or nitrogen atom optionally substituted with methyl, R6 has the meaning mentioned above.

The more preferable compounds are also compounds of formulas 1.2.2(1), 1.2.2(2), 1.2.2(3), 1.2.3(1), 1.2.3(2) and 1.2.3(3), their optical (R)-isomers—(R)-1.2.2(1), (R)-1.2.2 (2), (R)-1.2.2(3), (R)-1.2.3(1), and (S)-isomers—(S)-1.2.2 (1), (S)-1.2.2(2), (S)-1.2.2(3), (S)-1.2.3(1), or a pharmaceutically acceptable salt thereof,

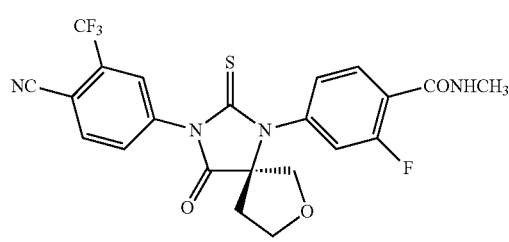

(R)-1.2.3(1)

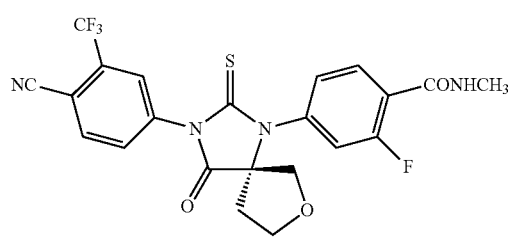

1.2.2(1): R6 = OCH₃;
1.2.2(2): R6 = OCH₂Ph;
1.2.2(3): R6 = OH;

(S)-1.2.3(1)

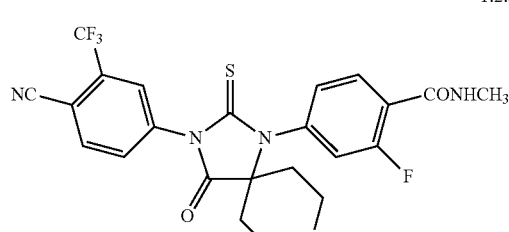

1.2.3(2)

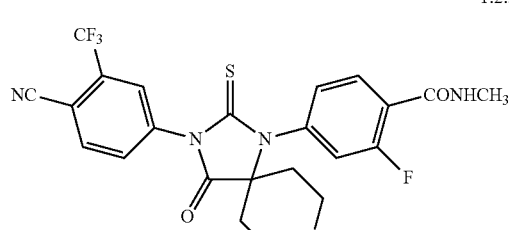

(R)-1.2.2(1): R6 = OCH₃;
(R)-1.2.2(2): R6 = OCH₂Ph;
(R)-1.2.2(3): R6 = OH;

1.2.3(3)

wherein R6 represents hydroxyl group optionally substituted with methyl or benzyl, The subject of the present invention is a method for preparation of compounds of the general formula 1.2 and optical (R)- and (S)-isomers thereof.

1,3-Diarylhydantoines of the general formula 1.2 are prepared by interaction of isothiocyanate 3.2 with the corresponding 4-(cyanomethyl)aminobenzamides 4.1 or (4-carbamoylphenylamino) acetic acids 4.2 according to scheme 1.

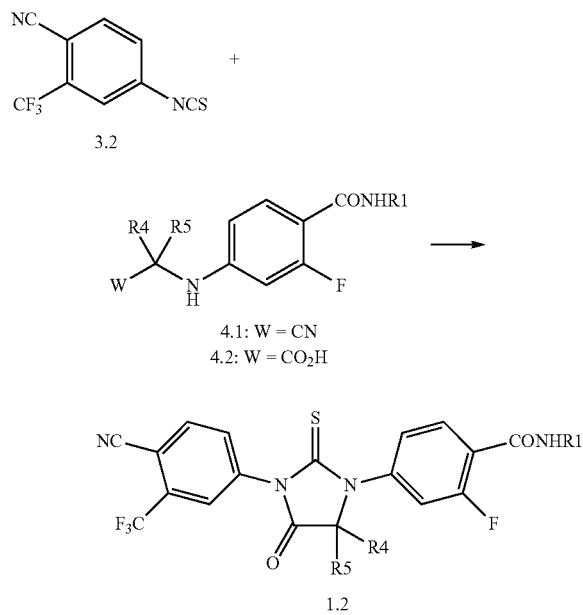

wherein:
R1, R4 and R5 have the above meanings.

Optically active cyclic N,N'-diarylthioureas, (R)-1.2 and (S)-1.2 isomers, are prepared either from the corresponding optically active (R)-4.1, (R)-4.2, (S)-4.1 and (S)-4.2 starting materials, or by resolution of racemic mixtures of cyclic N,N'-diarylthioureas 1.2 to enantiomers.

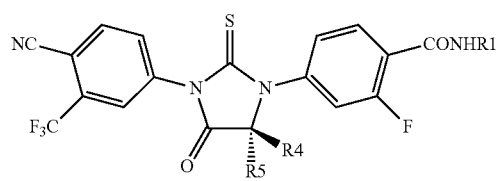

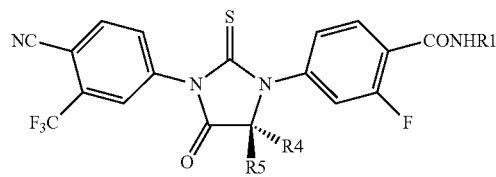

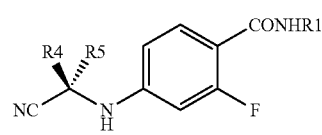

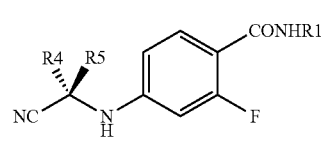

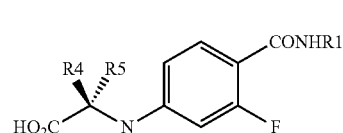

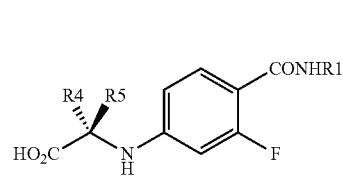

wherein:
R1, R4 and R5 have the above meanings.

1,3-Diaryltetrahydropyrimidin-2-ones of the general formula 1.3.1 are prepared by interaction of the corresponding N,N'-diarylureas of the general formula 2 with 1,3-dibromopropane according to scheme 2.

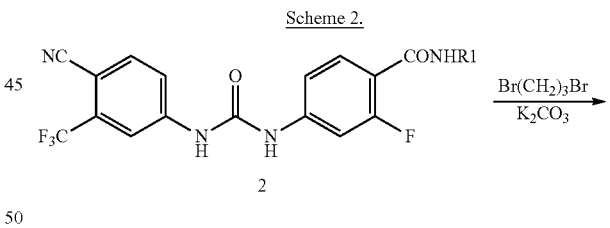

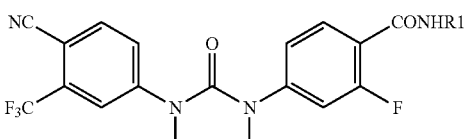

wherein:
R1 has the above meaning.

Compounds of the general formula 1.3.2 are prepared by interaction of isocyanate 3.1 or isothiocyanate 3.2 with the corresponding ethyl β-alaninates of the general formula 5 with subsequent cyclization of obtained ureas of the general formula 6 according to scheme 3.

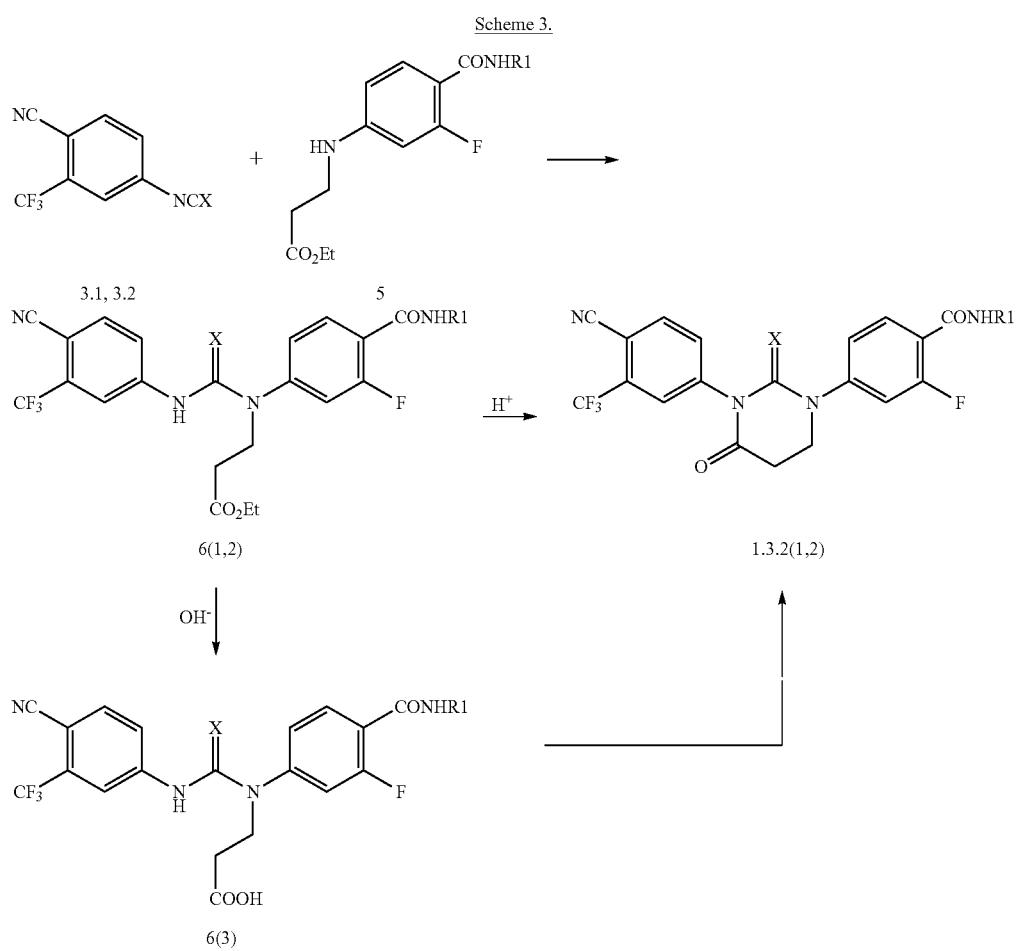

wherein:
X and R1 have the above meanings.

1,4-Diaryl[1,2,4]triazolidin-3,5-diones of the general formula 1.4 are prepared by interaction of the corresponding hydrazine 7 with isocyante 3.1 and subsequent condensation of the prepared semicarbazide 8 with diphosgene according to scheme 4.

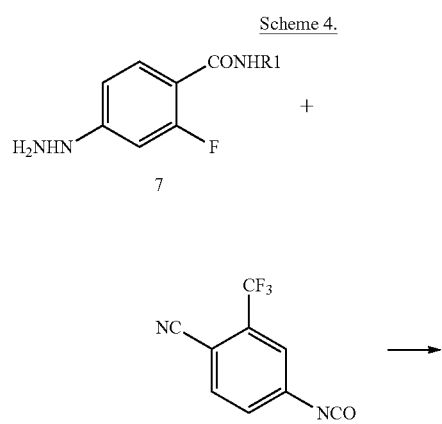

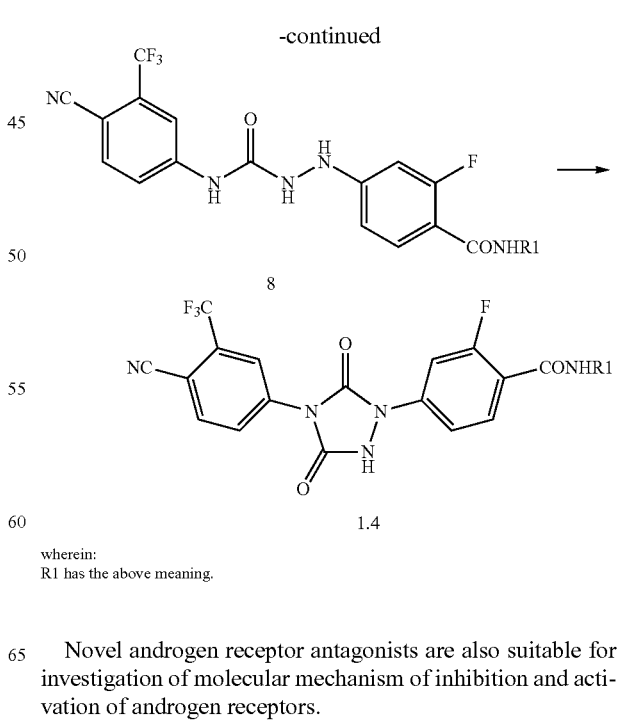

wherein:
R1 has the above meaning.

Novel androgen receptor antagonists are also suitable for investigation of molecular mechanism of inhibition and activation of androgen receptors.

Novel cyclic N,N'-diarylthioureas and N,N'-diarylureas of the general formula 1 are androgen receptor antagonists, at that their activity exceeds the activity of known androgen receptor antagonists, published in patent application WO2006124118, WO2007127010, and in *Drug Data Rep.*, 2009, 31(6), 609.

Besides, novel antagonist 1.2.3(1) is more than three times as less toxical as MDV3100 antagonist, because its maximum tolerated dose (MTD), determined in experiments with male mice of CD1 line is equel to MTD >100 mg/kg, whilst MTD for MDV3100 is about ~30 mg/kg.

The subject of the present invention is novel anticancer agent representing at least one cyclic N,N'-diarylthioureas or N,N'-diarylureas of the general formula 1.

The subject of the present invention is also a novel pharmaceutical composition for treating breast cancer disease comprising an effective amount of at least one cyclic N,N'-diarylthiourea compound of general formula 1.2, or an optical (R)- or (S)-isomer, or a pharmaceutically acceptable salt thereof, and further comprising a pharmaceutically acceptable carrier or an excipient,

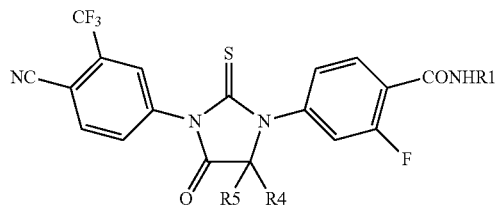

1.2 wherein:
R1 represents $C_1$-$C_3$ alkyl;
R4 and R5 represent hydrogen; or
R4 represents hydrogen, R5 represents methyl; or
R4 represents methyl, R5 represents $CH_2R6$ group in which R6 is $C_1$-$C_3$ alkoxycarbonyl, carboxyl, hydroxyl group optionally substituted with methyl or benzyl; or
R4 and R5 together with the carbon atom they are attached to form 5- or 6-membered saturated heterocycle including at least one oxygen atom or nitrogen atom optionally substituted with methyl.

A pharmaceutical composition may include pharmaceutically acceptable excipients. Pharmaceutically acceptable excipients mean diluents, auxiliary agents and/or carriers employing in the sphere of pharmaceutics. According to the invention the pharmaceutical composition in addition to the cyclic N,N'-diarylthiourea of the general formula 1.2, its optically active isomer or pharmaceutically acceptable salt may include other active components, among other things exhibiting anti-cancer activity, provided that they do not give rise to undesirable side-effects.

According to the present invention, if it is necessary to use the pharmaceutical composition in clinical practice it can be mixed up with various traditional pharmaceutical carries.

According to the present invention the carriers used in pharmaceutical compositions represent carriers which are applied in the sphere of pharmaceutics for preparation of commonly used forms including: binding agents, greasing agents, disintegrators, solvents, diluents, stabilizers, suspending agents, colorless agents, taste flavors are used for peroral forms; antiseptic agents, solubilizers, stabilizers are used in the forms for injections; base materials, diluents, greasing agents, antiseptic agents are used in local forms.

The purpose of the present invention is also the method for preparation of pharmaceutical compositions.

The object in view is achieved by mixing novel anti-cancer agent with an inert exicipient and/or solvent, the distinctive feature of which consists in utilization as anticancer agent, at least, one cyclic N,N'-diarylthiourea or N,N'-diarylurea of the general formula 1, or a optically active isomer or a pharmaceutically acceptable salt thereof.

In some embodiments of the present invention the pharmaceutical composition is in the form of a tablet, a capsule, or an injection placed in a pharmaceutically acceptable package intended for cancer treatment.

The subject of the present invention is also a method for treating a breast cancer in a subject comprising administering an effective dose of a pharmaceutical composition according to the instant invention to a subject in need thereof.

A composition or a medicament could be administered perorally or parenterally, for example, intravenously, subcutaneously, intraperitoneally or locally. The clinical dosage of the active component of the general formula 1.2 could be corrected depending on: therapeutic efficiency and bioavailability of the active ingredients in organism, rate of their exchange and deducing from organism, and also depending on the age, sex and the severity of the patient's symptoms; the daily dosage for adults falls within the range of about 10 to about 500 mg of the active ingredient, preferably of about 50 to about 300 mg. Therefore, according to the present invention in the process of preparation of a medicament from the pharmaceutical composition as units of dosage it is necessary to keep in mind the above effective dosage, so that each unit of dosage should contain of about 10 to about 500 mg of the compound of the general formula 1, preferably 50~300 mg. In accordance with the recommendation of physician or pharmacist the above dosage can be taken several times during the definite time intervals (preferably—from one to six times).

BEST EMBODIMENT OF THE INVENTION

Figure 2:
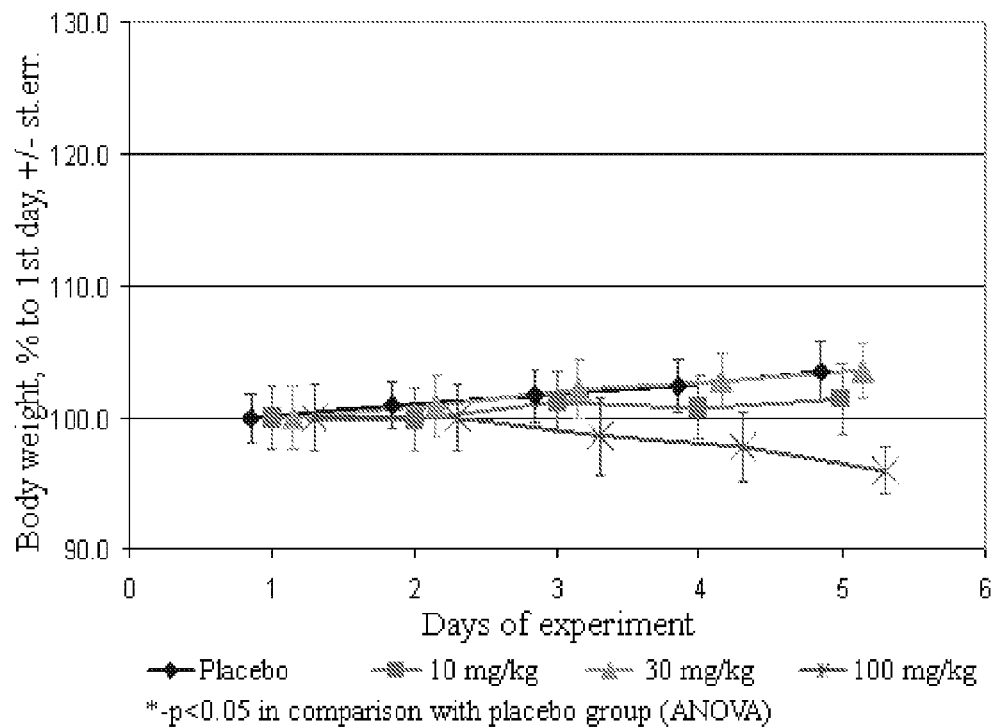
Figure 3:
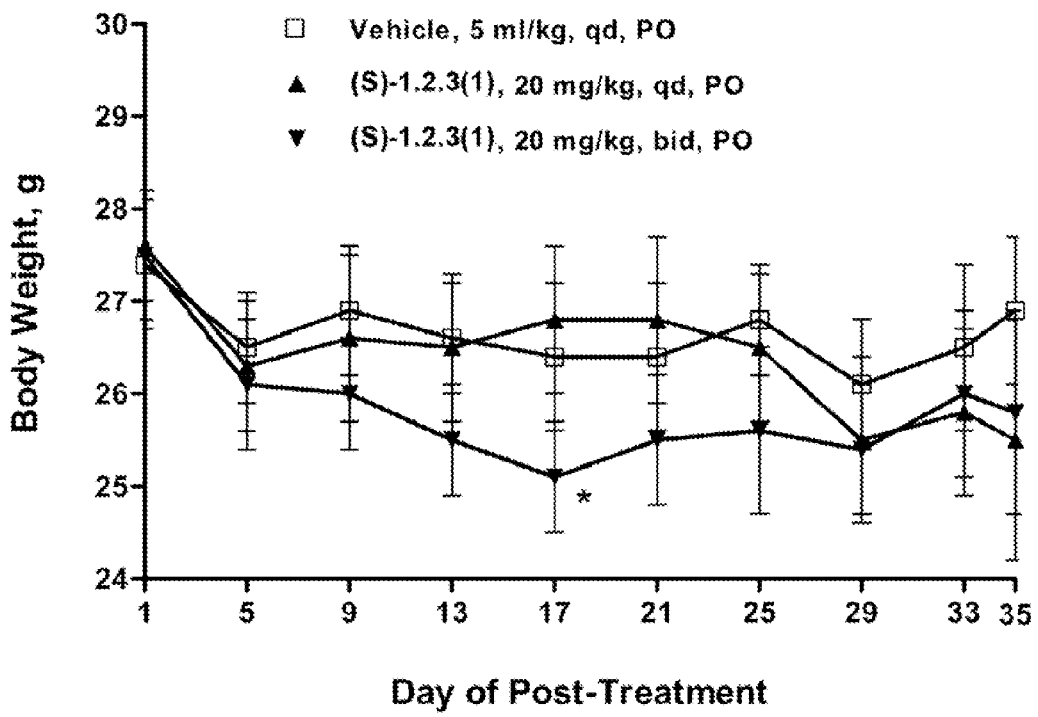
Figure 4:
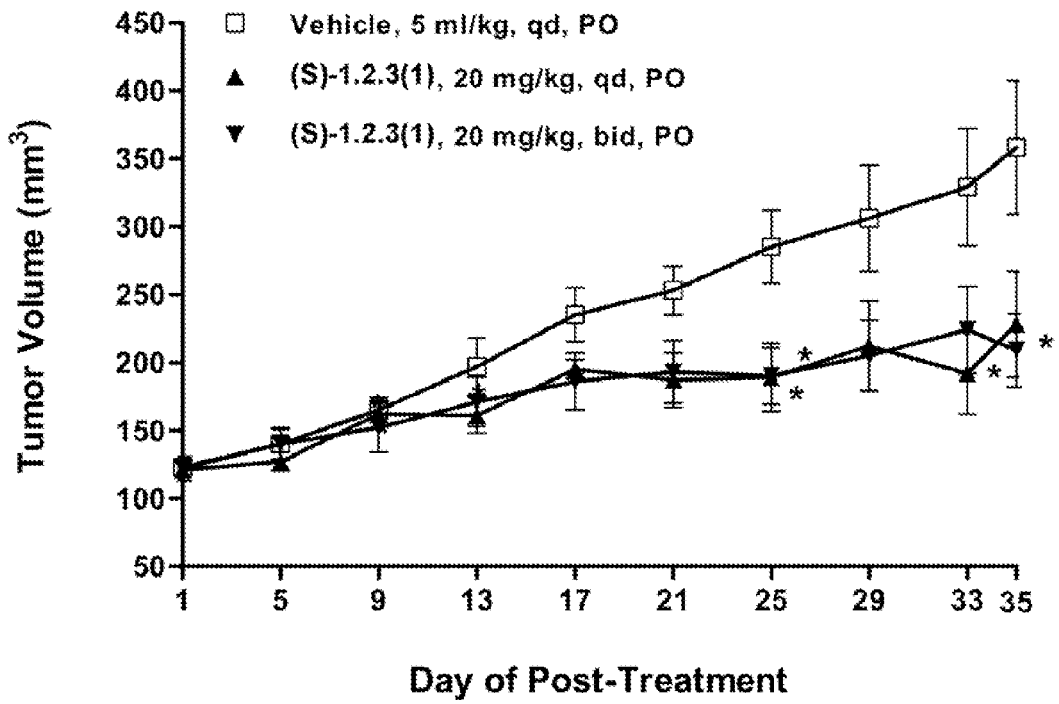

The invention is illustrated by the following drawings.
FIG. 1. Weight change of male mice at peroral introduction of compound 1.2.3(1).
FIG. 2. Weight change of male mice at peroral introduction of compound MDV3100.
FIG. 3. Dynamics of changes in weight of the animals during the use of (S)-1.2.3(1) at a dose of 20 mg/kg once daily (qd) and twice daily (bid), and control animals.
FIG. 4. Dynamics of changes in tumor volume of animals during the use of (S)-1.2.3(1) at a dose of 20 mg/kg once daily (qd) and twice daily (bid), and control animals. *–T/C≤42%

The examples given below describe synthesis of N,N'-diarylthioureas and N,N'-diarylureas and data of their biological investigation, which illustrate but not limit the scope of the invention.

EXAMPLE 1

Synthesis of N-methyl-4-{4-oxo-2-thioxo-3-[3-(trifluoromethyl)-4-cyanophenyl]imidazolidin-1-yl}-2-fluorobenzamide 1.2(1). Glycine (80 mg, 1.07 mmol) and $K_2CO_3$ (207 mg, 1.5 mmol) were added to solution of 4-iodo-N-methyl-2-fluorobenzamide (279 mg, 1 mmol) in DMF (3 ml). The reaction mixture was stirred at 140° C. for 18 min. in microwave oven, cooled, diluted with AcOEt (10 ml) and water (10 ml), neutralized with HCl to pH 2-3, organic layer was separated, water layer was extracted with AcOEt (5×20 ml). The combined extracts were washed with brine, dried over $Na_2SO_4$ and evaporated in vacuo. The product was isolated by column chromatography on SiO$_2$. It gave N-(4-methylcarbamoyl-2-fluorophenyl)glycine 4.2(1) (R1=CH$_3$, R4=R5=H,). A solution of N-(4-methylcarbamoyl-2-fluorophenyl)glycine 4.2(1) (113 mg, 0.5 mmol) and 4-isothiocyanato-2-(trifluoromethyl)benzonirile 3.2 (174 mg, 1.0 mmol) in DMF (2 ml) was stirred at 90° C. for 12 h. The reaction mixture was evaporated in vacuo, and N-methyl-4-{4-oxo-2-thioxo-3-[3-(trifluoromethyl)-4-cyanophenyl]-imidazolidin-1-yl}-2-fluorobenzamide 1.2(1), was isolated by HPLC method, LCMS (M+H)$^+$437.

EXAMPLE 2

General method for synthesis of N-methyl-4-{5-methyl-4-oxo-2-thioxo-3-[3-(trifluoromethyl)-4-cyanophenyl]imidazolidin-1-yl}-2-fluorobenzamide 1.2(2), N-methyl-4-{(S)-5-methyl-4-oxo-2-thioxo-3-[3-(trifluoromethyl)-4-cyanophenyl]imidazolidin-1-yl}-2-fluorobenzamide (S)-1.2(2) and N-methyl-4-{(R)-5-methyl-4-oxo-2-thioxo-3-[3-(trifluoromethyl)-4-cyanophenyl]imidazolidin-1-yl}-2-fluorobenzamide (R)-1.2(2).

(D,L)-, (D)- or (L)-Alanine (347 mg, 7.8 mmol) and Cs$_2$CO$_3$ (2.54 g, 7.8 mmol) were added to the solution of N-methyl-2,4-difluorobenzamide (667 mg, 3.9 mmol) in DMSO (3 ml). The reaction mixture was stirred in closed vial at 90° C. for 18 h. Cooled mixture was diluted with isopropanol, neutralized with HCl (1.36 ml, 15.6 mmol), filtered, evaporated in vacuo, and by HPLC method N-(4-methylcarbamoyl-3-fluorophenyl)alanine 4.2(2) (R1=CH$_3$, R4=H, R5=CH$_3$), (S)—N-(4-methylcarbamoyl-3-fluorophenyl)alanine (S)-4.2(2) or (R)—N-(4-methylcarbamoyl-3-fluorophenyl)alanine (R)-4.2(2) were isolated. LCMS (M+H)$^+$ 241. $^1$H NMR (DMSO-d$_6$, 400 MHz): 12.66 (br. s, 1H), 7.62 (m, 1H), 7.45 (t, J=8.8 Hz, 1H), 6.67 (br. d, J=7.2 Hz, 1H), 6.42 (dd, J$_1$=8.4 Hz, J$_2$=2.0 Hz, 1H), 6.29 (dd, J$_1$=14.8 Hz, J$_2$=2.0 Hz, 1H), 4.03 (m, 1H), 2.73 (d, J=4.4 Hz, 3H), 1.37 (d, J=7.2 Hz, 3H). Solution of amine 4.2(2), (S)-4.2(2) or (R)-4.2(2) (110 mg, 0.46 mmol) and 4-isothiocyanato-2-(trifluoromethyl)-benzonitrile 3.2 (144 mg, 0.55 mmol) in DMF (2 ml) was stirred at 90° C. for 12 h in microwave oven, then additional portion of 4-isothiocyanato-2-(trifluoromethyl)-benzonitrile 3.2 (50 mg, 0.19 mmol) was added and stirring was continued for another 12 h. The reaction mixture was evaporated in vacuo, and by HPLC method N-methyl-4-{5-methyl-4-oxo-2-thioxo-3-[3-(trifluoromethyl)-4-cyanophenyl]imidazolidin-1-yl}-2-fluorobenzamide 1.2(2), or N-methyl-4-{(S)-5-methyl-4-oxo-2-thioxo-3-[3-(trifluoromethyl)-4-cyanophenyl]imidazolidin-1-yl}-2-fluorobenzamide (S)-1.2(2) or N-methyl-4-{(R)-5-methyl-4-oxo-2-thioxo-3-[3-(trifluoromethyl)-4-cyanophenyl]imidazolidin-1-yl}-2-fluorobenzamide (R)-1.2(2) were isolated, respectively. The apparent inhibition constant of androgen receptors (K$_i$) for these compounds are: K$_i^{1.2(2)}$=140.2 nM, K$_i^{(S)-1.2(2)}$=106.7 nM и K$_i^{(R)-1.2(2)}$=73.6 nM, respectively. LCMS (M+H)$^+$ 451. $^1$H NMR (CDCl$_3$, 400 MHz): 8.28 (t, J=8.6 Hz, 1H), 8.01 (d, J=8.0 Hz, 1H), 7.94 (d, J=1.2 Hz, 1H), 7.81 (dd, J$_1$=8.0 Hz, J$_2$=1.2 Hz, 1H), 7.48 (dd, J$_1$=12.4 Hz, J$_2$=1.6 Hz, 1H), 7.36 (dd, J$_1$=8.4 Hz, J$_2$=1.6 Hz, 1H), 6.72 (br. m, 1H), 4.83 (q, J=7.2 Hz, 1H), 3.08 (d, J=4.8 Hz, 3H), 1.60 (d, J=7.2 Hz, 3H).

EXAMPLE 3

Synthesis of N-methyl-4-{2-thio-3-[3-(trifluoromethyl)-4-cyanophenyl]-hydantoin-1-yl}-2-fluorobenzamides 1.2.2 and 1.2.3 (general method). Solution of the corresponding N-methyl-2-fluoro-4-[(1-cyanomethyl)amino]benzamide 4.1 (0.75 mmol) and 4-isothiocyanato-2-(trifluoromethyl) benzonitrile 3.2 (342 mg, 1.5 mmol) in DMF (3 ml) was stirred at 110° C. for 12 h in microwave oven. The reaction mixture was dissolved in MeOH (30 ml), 1N HCl (7.5 ml) was added and the resultant mixture was boiled for 1.5 h. The solution was evaporated in vacuo, treated with water, the solid was filtered off, washed with water and dried in vacuo. The product was isolated by HPLC method. It gave: N-methyl-4-[5-methyl-5-(methoxymethyl)-4-oxo-2-thioxo-3-[3-(trifluoromethyl)-4-cyanophenyl]-imidazolidin-1-yl]-2-fluorobenzamide 1.2.2(1), K$_i^{1.2.2(1)}$=115.9 nM, which was separated to enantiomers by means of high pressure liquid chromatography on Chiralpak HD-H 25×1 cm (Chiral Technologies Inc., USA). Mixture of 80% n-hexane, 20% 2-propanol and 0.02% triethylamine was used as eluent. Flowrate was 4 ml/min. It gave optically pure isomers (R)-1.2.2(1) and (S)-1.2.2(1), K$_i^{(R)-1.2.2(1)}$=53.3 nM, K$_i^{(S)-1.2.2(1)}$=721.5 nM. LCMS (M+H)$^+$ 495. $^1$H NMR (CDCl$_3$, 400 MHz): 8.28 (t, J=8.4 Hz, 1H), 7.99 (d, J=8.0 Hz, 1H), 7.92 (s, 1H), 7.80 (d, J=8.0 Hz, 1H), 7.29 (dd, J$_1$=8.8 Hz, J$_2$=1.2 Hz, 1H), 7.21 (dd, J$_1$=11.6 Hz, J$_2$=1.2 Hz, 1H), 6.72 (q, J=4.4 Hz, 1H), 3.71 (d, J=10.0 Hz, 1H), 3.43 (s, 3H), 3.35 (d, J=10.0 Hz, 1H), 3.09 (d, J=4.4 Hz, 3H), 1.52 (s, 3H);

N-methyl-4-{5-[(benzyloxy)methyl]-5-methyl-4-oxo-2-thioxo-3-[3-(trifluoromethyl)-4-cyanophenyl]imidazolidin-1-yl}-2-fluorobenzamide 1.2.2(2). LCMS (M+H)$^+$ 571. $^1$H NMR (CDCl$_3$, 400 MHz): 8.22 (t, J=8.4 Hz, 1H), 7.96 (d, J=8.0 Hz, 1H), 7.86 (s, 1H), 7.70 (dd, J$_1$=8.0 Hz, J$_2$=1.2 Hz, 1H), 7.39 (m, 3H), 7.29 (m, 2H), 7.25 (dd, J$_1$=8.4 Hz, J$_2$=1.6 Hz, 1H), 7.18 (dd, J$_1$=8.4 Hz, J$_2$=1.6 Hz, 1H), 6.71 (q, J=4.8 Hz, 1H), 4.59 (m, 2H), 3.79 (d, J=10.2 Hz, 1H), 3.45 (d, J=10.2 Hz, 1H), 3.08 (d, J=4.8 Hz, 3H), 1.51 (s, 3H);

ethyl {4-methyl-3-(4-methylcarbamoyl-3-fluorophenyl)-5-oxo-2-thioxo-1-[3-(trifluoromethyl)-4-cyanophenyl]imidazolidin-4-yl}acetate 1.2.2(4) (R1=CH$_3$, R4=CH$_3$, R5=CH$_2$COOC$_2$H$_5$). LCMS (M+H)$^+$ 536. $^1$H NMR (CDCl$_3$, 400 MHz): 8.26 (t, J=8.4 Hz, 1H), 8.01 (d, J=8.0 Hz, 1H), 8.00 (s, 1H), 7.90 (dd, J$_1$=8.0 Hz, J$_2$=1.6 Hz, 1H), 7.18 (dd, J$_1$=8.0 Hz, J$_2$=1.6 Hz, 1H), 7.10 (dd, J$_1$=8.0 Hz, J$_2$=1.6 Hz, 1H), 6.78 (q, J=4.8 Hz, 1H), 4.26 (m, 1H), 3.13 (d, J=18.0 Hz, 1H), 3.09 (d, J=4.8 Hz, 3H), 2.64 (d, J=18.0 Hz, 1H), 1.67 (s, 3H), 1.31 (t, J=7.0 Hz, 3H);

N-methyl-4-{4-oxo-2-thioxo-3-[3-(trifluoromethyl)-4-cyanophenyl]-7-oxa-1,3-diazaspiro[4.4]non-1-yl}-2-fluorobenzamide 1.2.3(1), K$_i^{1.2.3(1)}$=33.9 nM. LCMS (M+H)$^+$ 493. $^1$H NMR (CDCl$_3$, 400 MHz): 8.30 (t, J=8.4 Hz, 1H), 8.02 (d, J=8.4 Hz, 1H), 7.98 (d, J=1.6 Hz, 1H), 7.85 (dd, J$_1$=8.4 Hz, J$_2$=1.6 Hz, 1H), 7.34 (dd, J$_1$=8.4 Hz, J$_2$=1.6 Hz, 1H), 7.25 (dd, J$_1$=11.8 Hz, J$_2$=1.6 Hz, 1H), 6.78 (q, J=4.4 Hz, 1H), 4.43 (d, J=10.0 Hz, 1H), 4.16 (d, J=10.0 Hz, 1H), 3.96 (m, 1H), 3.75 (m, 1H), 3.09 (d, J=4.4 Hz, 3H), 2.74 (m, 1H), 2.48 (m, 1H);

N-methyl-4-{4-oxo-2-thioxo-3-[3-(trifluoromethyl)-4-cyanophenyl]-8-oxa-1,3-diazaspiro[4.5]dec-1-yl}-2-fluorobenzamide 1.2.3(2). LCMS (M+H)$^+$ 507. $^1$H NMR (CDCl$_3$, 400 MHz): 8.32 (t, J=8.4 Hz, 1H), 8.01 (d, J=8.0 Hz, 1H), 7.95 (s, 1H), 7.83 (d, J=8.0 Hz, 1H), 7.20 (d, J=8.4 Hz, 1H), 7.10 (d, J=8.0 Hz, 1H), 6.73 (br. m, 1H), 4.18 (m, 2H), 3.94 (m, 2H), 3.09 (d, J=4.4 Hz, 3H), 2.07 (m, 4H);

N-methyl-4-{8-methyl-4-oxo-2-thioxo-3-[3-(trifluoromethyl)-4-cyanophenyl]-1,3,8-triazaspiro[4.5]dec-1-yl}-2-fluorobenzamide 1.2.3(3). K$_i^{1.2.3(3)}$=39.2 nM, IC$_{50}$=170 nM. LCMS (M+H)$^+$ 520. $^1$H NMR (DMSO-d$_6$, 400 MHz): 10.09 (br. s, 1H), 8.48 (q, J=4.4 Hz, 1H), 8.43 (d, J=8.4 Hz, 1H), 8.29 (s, 1H), 8.11 (d, J=8.4 Hz, 1H), 7.84 (t, J=8.0 Hz, 1H), 7.42 (d, J=10.4 Hz, 1H), 7.30 (d, J=8.0 Hz, 1H), 3.50 (m, 4H), 2.80 (d, J=4.4 Hz, 3H), 2.78 (s, 3H), 2.72 (d, J=14.0 Hz, 1H), 2.16 (m, 2H).

Such salts of the compounds of general formula 1.2.3 of the present invention as hydrochloride, hydrobromide, phosphate, nitrate, perchlorate, sulfate, acetate could be formed by methods well known in the art. For example, the compound 1.2.3(3) was dissolved in dichloromethane and a saturated solution of HCl in dioxane was added. The N-methyl-4-{8-methyl-4-oxo-2-thioxo-3-[3-(trifluoromethyl)-4-cyanophenyl]-1,3,8-triazaspiro[4.5]dec-1-yl}-2-fluorobenzamide hydrochloride salt 1.2.3(3)*HCl obtained in the precipitate was washed with dioxane, evaporated and dried. LCMS (M+H)$^+$ 520.

EXAMPLE 4

Synthesis of N-methyl-4-[5-(hydroxymethyl)-5-methyl-4-oxo-2-thioxo-3-[3-(trifluoromethyl)-4-cyanophenyl]imidazolidin-1-yl]-2-fluorobenzamide 1.2.2(3). BBr$_3$ (53 mkl, 0.55 mmol) was added dropwise to solution of N-methyl-4-[5-methyl-5-(methoxymethyl)-4-oxo-2-thioxo-3-[3-(trifluoromethyl)-4-cyanophenyl]imidazolidin-1-yl]-2-fluorobenzamide (55 mg, 0.11 mmol) in CH$_2$Cl$_2$ (1.5 ml) in argon atmosphere at −78° C. The reaction mixture was stirred at −78° C. for 3 h and then for another 3 h at room temperature. After the reaction was completed the excess of BBr$_3$ was neutralized by addition of 5% Na$_2$CO$_3$ solution (10 ml), the product was extracted with AcOEt, dried over Na$_2$SO$_4$, evaporated in vacuo, and by HPLC method N-methyl-4-[5-(hydroxymethyl)-5-methyl-4-oxo-2-thioxo-3-[3-(trifluoromethyl)-4-cyanophenyl]imidazolidin-1-yl]-2-fluorobenzamide 1.2.2(3) was isolated, $K_i^{1.2.2(3)}$=46.3 nM, $^1$H NMR (DMSO-d$_6$, 400 MHz): 8.43 (br. m, 1H), 8.39 (d, J=8.4 Hz, 1H), 8.13 (s, 1H), 7.98 (d, J=8.4 Hz, 1H), 7.78 (t, J=8.0 Hz, 1H), 7.42 (d, J=10.8 Hz, 1H), 7.37 (d, J=8.0 Hz, 1H), 5.93 (t, J=4.4 Hz, 1H), 3.81 (dd, J$_1$=11.6 Hz, J$_2$=4.4 Hz, 1H), 3.45 (dd, J$_1$=11.6 Hz, J$_2$=5.0 Hz, 1H), 2.79 (d, J=4.0 Hz, 3H), 1.38 (s, 3H).

EXAMPLE 5

Synthesis of {4-methyl-3-(4-methylcarbamoyl-3-fluorophenyl)-5-oxo-2-thioxo-1-[3-(trifluoromethyl)-4-cyanophenyl]imidazolidin-4-yl}acetic acid 1.2.2(5) (R1=CH$_3$, R4=CH$_3$, R5=CH$_2$COOH). Solution of NaOH (7 mg, 0.172 mmol) in water (0.5 ml) was added to the solution of ester (46 mg, 0.086 mmol) 1.2.2(4) in alcohol (2 ml), and the reaction mixture was stirred for 12 h (LCMS control). The solvent was evaporated, isopropanol (2 ml) and HCl (15 mkl, 0.172 mmol) were added, filtered and evaporated again in vacuo. {4-Methyl-3-(4-methylcarbamoyl-3-fluorophenyl)-5-oxo-2-thioxo-1-[3-(trifluoromethyl)-4-cyanophenyl]imidazolidin-4-yl}acetic acid 1.2.2(5) was isolated by HPLC method. LCMS (M+H)$^+$ 469. $^1$H NMR (DMSO-d$_6$, 400 MHz): 13.31 (br. s, 1H), 8.44 (m, 2H), 8.10 (s, 1H), 7.95 (d, J=7.6 Hz, 1H), 7.81 (t, J=8.0 Hz, 1H), 7.25 (d, J=10.8 Hz, 1H), 7.19 (d, J=8.0 Hz, 1H), 3.16 (d, J=17.6 Hz, 1H), 2.79 (d, J=3.6 Hz, 3H), 2.70 (d, J=17.6 Hz, 1H), 1.59 (s, 3H).

EXAMPLE 6

Synthesis of 4-[3-[3-(trifluoromethyl)-4-cyanophenyl]-2-oxo-tetrahydro-pyrimidin-1(2H)-yl]-N-methyl-2-fluorobenzamide 1.3.1. K$_2$CO$_3$ (109 mg, 0.79 mmol) and 1,3-dibromopropane (32 mkl, 0.32 mmol) were added to a solution of 4-[4-cyano-3-(trifluoromethyl)-phenylcarbamoylamino]-N-methyl-2-fluorobenzamide (100 mg, 0.26 mmol) 2 in DMF (2 ml). Mixture was stirred at 90° C. In 18 h another portion of K$_2$CO$_3$ (109 mg) and 1,3-dibromopropane (32 mkl) were added and stirring was continued at the same temperature. Addition was repeated by 2 more times. After the reaction was completed the mixture was evaporated in vacuo, the residue was dissolved in chloroform, washed with water, dried over Na$_2$SO$_4$, the solvent was evaporated. The product was isolated by colomn chromatography on SiO$_2$ (eluent—AcOEt). LCMS (M+H)$^+$ 421. $^1$H NMR (DMSO-d$_6$, 400 MHz): 8.17 (br. m, 1H), 8.13 (d, J=8.4 Hz, 1H), 8.07 (d, J=2.0 Hz, 1H), 7.83 (dd, J$_1$=8.4 Hz, J$_2$=2.0 Hz, 1H), 7.62 (t, J=8.4 Hz, 1H), 7.38 (dd, J$_1$=12.4 Hz, J$_2$=2.0 Hz, 1H), 7.29 (dd, J$_1$=8.4 Hz, J$_2$=2.0 Hz, 1H), 3.90 (t, J=5.8 Hz, 2H), 3.81 (t, J=5.8 Hz, 2H), 2.77 (d, J=4.8 Hz, 3H), 2.21 (m, 2H).

EXAMPLE 7

Synthesis of N-methyl-4-{[3-(trifluoromethyl)-4-cyanophenyl]-2,4-dioxo-tetrahydropyrimidin-1(2H)-yl}benzamide 1.3.2(1), (X=O, R1=CH$_3$). Ethyl acrylate (8 g, 80 mmol) and DBU (0.81 g, 5.4 mmol) were added to a solution of 4-amino-N-methyl-2-fluorobenzamide (9 g, 53.6 mmol) in DMSO (90 ml) and stirring was continued for 24 h at 70° C. (LCMS control). The reaction mixture was subjected to lyophilization, the residue was recrystallized from aqueous alcohol. It gave ethyl N-[4-(methylcarbamoyl)-3-fluorophenyl]-β-alaninate 5. LCMS (M+H)$^+$ 269. $^1$H NMR (DMSO-d$_6$, 400 MHz) δ 7.57 (br. s, 1H), 7.48 (t, J=8.8 Hz, 1H), 6.47 (br. s, 1H), 6.42 (d, J=8.8 Hz, 1H), 6.33 (d, J=14.8 Hz, 1H), 4.07 (q, J=7.2 Hz, 2H), 3.32 (br. m, 2H), 2.73 (d, J=4.4 Hz, 3H), 2.55 (t, J=6.4 Hz, 2H), 1.18 (t, J=7.2 Hz, 3H). The solution of 4-isocyanato-2-(trifluoromethyl)benzonitrile (425 mg, 1.87 mmol) 3.1 and ethyl N-[4-(methylcarbamoyl)-3-fluorophenyl]-β-alaninate (500 mg, 1.87 mmol) 5 (R1=CH$_3$) in CH$_2$Cl$_2$ (10 ml) was stirred for 5 h. The reaction mixture was evaporated in vacuo, and the product was isolated by colomn chromatography on SiO$_2$ (eluent—n-hexane:AcOEt:Et$_3$N=1:1:0.03). It gave ethyl N-[4-(methylcabamoyl)-3-fluorophenyl]-N-{[3-(trifluoromethyl)-4-cyanophenyl]-carbamoyl}-β-alaninate 6(1) (R1=CH$_3$, X=O). LCMS (M+H)$^+$ 481. HCl (2.5 ml) was added to the solution of ethyl N-[4-(methylcabamoyl)-3-fluorophenyl]-N-{[3-(trifluoromethyl)-4-cyanophenyl]-carbamoyl}-β-alaninate (500 mg, 1.04 mmol) 6(1) in AcOH (5 ml) and the resultant mixture was stirred for 15 h. The reaction mixture was poured into water, the product was extracted with EtOAc. Organic layer was dried over Na$_2$SO$_4$, evaporated in vacuo and by means of colomn chromatography on SiO$_2$ (eluent—n-hexane:AcOEt=1:1) N-methyl-4-{[3-(trifluoromethyl)-4-cyanophenyl]-2,4-dioxo-tetrahydropyrimidin-1(2H)-yl}benzamide 1.3.2, (X=O, R1=CH$_3$) was isolated; $K_i^{1.3.2}$(1)=85.6 nM, LCMS (M+H)$^+$ 435. $^1$H NMR (DMSO-d$_6$, 400 MHz): δ 8.29 (d, J=7.6 Hz, 1H), 8.23 (br. m, 1H), 8.11 (s, 1H), 7.89 (d, J=2.0 Hz, 1H), 7.67 (t, J=8.4 Hz, 1H), 7.39 (d, J=12.4 Hz, 1H), 7.33 (d, J=8.4 Hz, 1H), 4.02 (t, J=6.4 Hz, 2H), 3.03 (t, J=6.4 Hz, 2H), 2.77 (d, J=4.4 Hz, 3H).

EXAMPLE 8

Synthesis of N-methyl-4-{[3-(trifluoromethyl)-4-cyanophenyl]-4-oxo-2-thioxo-tetrahydropyrimidin-1(2H)-yl}benzamide 1.3.2(2), (X=S, R1=CH$_3$). A solution of 4-isothiocyanato-2-(trifluoromethyl)benzonitrile (320 mg, 1.51 mmol) 3.2 and ethyl N-[4-(methylcarbamoyl)-3-fluorophenyl]-β-alaninate (404 mg, 1.51 mmol) 5 (R1=CH$_3$) in DMF (8 ml) was heated at 60° C. in microwave stove for 8 h.

The reaction mixture was evaporated in vacuo, and by means of colomn chromatography on $SiO_2$ (eluent—n-hexane:AcOEt=1:2) ethyl N-[4-(methylcarbamoyl)-3-fluorophenyl]-N-{[3-(trifluoromethyl)-4-cyanophenyl]thiocarbamoyl}-β-alaninate 6(2) (R1=$CH_3$, X=S) was isolated. LCMS (M+H)$^+$ 497. A solution of NaOH (32 mg, 0.8 mmol) in water (0.25 ml) was added to a solution of ester (200 mg, 0.4 mmol) 6(2) in alcohol (1 ml), and the resultant mixture was stirred at 80° C. for 2 h (LCMS control), cooled and neutralized with HCl (69 mkl, 0.8 mmol), evaporated in vacuo, the residue was extracted with hot isopropanol and evaporated in vacuo again. It gave N-[4-(methylcarbamoyl)-3-fluorophenyl]-N-{[3-(trifluoromethyl)-4-cyanophenyl]thiocarbamoyl}-β-alanine 6(3) (R1=$CH_3$, X=S). LCMS (M+H)$^+$ 469. TBTU (86 mg, 0.36 mmol) and diisopropylethylamine (110 mg, 0.84 mmol) were added to the solution of the prepared acid (114 mg, 0.24 mmol) 6(3) in DMF (1.5 ml). The reaction mixture was stirred at 45° C. for 15 h. When the reaction was completed (LCMS control) the solution was poured into water and extracted with EtOAc. The organic layer was dried over $Na_2SO_4$, evaporated in vacuo and by HPLC method N-methyl-4-{[3-(trifluoromethyl)-4-cyanophenyl]-4-oxo-2-thioxo-tetrahydropyrimidin-1(2H)-yl}-2-fluorobenzamide 1.3.2(2) (R1=$CH_3$, X=S) was isolated; $K_i^{1.3.2(2)}$=95.2 nM. LCMS (M+H)$^+$ 451. $^1$H NMR (DMSO-$d_6$, 400 MHz): 8.35 (q, J=4.4 Hz, 1H), 8.27 (d, J=8.0 Hz, 1H), 8.06 (d, J=1.6 Hz, 1H), 7.83 (dd, $J_1$=8.0 Hz, $J_2$=1.6 Hz, 1H), 7.71 (t, J=8.2 Hz, 1H), 7.42 (dd, $J_1$=11.0 Hz, $J_2$=1.8 Hz, 1H), 7.33 (dd, $J_1$=8.2 Hz, $J_2$=1.8 Hz, 1H), 4.13 (t, J=6.8 Hz, 2H), 3.17 (t, J=6.8 Hz, 2H), 2.78 (d, J=4.4 Hz, 3H).

EXAMPLE 9

Synthesis of N-methyl-2-fluoro-4-[4-[3-(trifluoromethyl)-4-cyanophenyl]-3,5-dioxo-1,2,4-triazolidin-1-yl]benzamide 1.4 (R1=$CH_3$). 2.5M Solution of $NaNO_2$ (2.38 ml) was added dropwise to a solution of 4-amino-N-methyl-2-fluorobenzamide (1 g, 5.95 mmol) in $_B$ 5N HCl (3.1 ml), so that the temperature of the reaction mixture did not exceed 5° C. The mixture was stirred for additional 30 min at the same temperature, after that the prepared solution was added drop by drop to a suspension of $SnCl_2*2H_2O$ (4.03 g, 17.9 mmol) in HCl (4.2 ml) at 0° C., and stirring was continued for 2 h at the same temperature. Precipitated solid was filtered off, dissolved in water (40 ml) and NaOH was added to strongly basic reaction. The mixture was extracted with ether (3*100 ml), dried over $MgSO_4$ and evaporated in vacuo. It gave 4-hydrazino-N-methyl-2-fluorobenzamide 7 (R1=$CH_3$). LCMS (M+H)$^+$ 184. $^1$H NMR (CDCl$_3$, 400 MHz): 7.96 (t, J=8.4 Hz, 1H), 6.64 (br. m, 1H), 6.60 (t, J=1.6 Hz, 1H), 6.57 (dd, $J_1$=7.2 Hz, $J_2$=2.0 Hz, 1H), 5.60 (br. s, 1H), 3.66 (br. s, 2H), 3.00 (dd, $J_1$=4.8 Hz, $J_2$=1.2 Hz, 1H). The solution of 4-isocyanato-2-(trifluoromethyl)benzonitrile (59 mg, 0.27 mmol) 3.1 in dioxane (2 ml) was added to a solution of 4-hydrazino-N-methyl-2-fluorobenzamide (54 mg, 0.29 mmol) 7 in dioxane (3 ml), and the resultant mixture was stirred for 2 h. Then dioxane was distilled in vacuo, the residue was crumbled with ether, filtered off and dried in vacuo. It gave 2-[(4-methylcarbamoyl)-3-fluorophenyl]-N-[3-(trifluoromethyl)-4-cyanophenyl]-hydrazine carboxamide 8(1) (R1=$CH_3$). LCMS (M+H)$^+$ 405. $^1$H NMR (DMSO-$d_6$, 400 MHz): 9.65 (br. s, 1H), 8.72 (br. s, 1H), 8.37 (s, 1H), 8.25 (br. s, 1H), 8.03 (br. m, 1H), 7.88 (d, J=8.8 Hz, 1H), 7.58 (m, 2H), 6.63 (d, J=8.4 Hz, 1H), 6.48 (d, J=14.0 Hz, 1H), 2.77 (d, J=4.4 Hz, 3H). Triethylamine (56 mkl, 0.4 mmol) and diphosgene (27 mkl, 0.22 mmol) were added one after another to 2-[(4-methylcarbamoyl)-3-fluorophenyl]-N-[3-(trifluoromethyl)-4-cyanophenyl]-hydrazine carboxamide (80 mg, 0.2 mmol) 8(1) in dichloroethane (2 ml). The reaction mixture was stirred in a closed vial at 80° C. for 15 h. The solvent was evaporated in vacuo and the residue was subjected to chromatography on $SiO_2$ (eluent—$CH_2Cl_2$:MeOH, gradient from 100:1 till 20:1). It gave N-methyl-2-fluoro-4-[4-[3-(trifluoromethyl)-4-cyanophenyl]-3,5-dioxo-1,2,4-triazolidin-1-yl]benzamide 1.4 (R1=$CH_3$). $K_i^{1.4}$=55.2 nM, LCMS (M+H)$^+$ 422. $^1$H NMR (DMSO-$d_6$, 400 MHz): 11.53 (s, 1H), 8.22 (br. m, 1H), 8.16 (d, J=8.8 Hz, 1H), 7.99 (dd, $J_1$=8.8 Hz, $J_2$=1.6 Hz, 1H), 7.95 (d, J=1.6 Hz, 1H), 7.81 (t, J=8.4 Hz, 1H), 7.69 (dd, $J_1$=8.8 Hz, $J_2$=2.0 Hz, 1H), 7.62 (dd, $J_1$=12.0 Hz, $J_2$=2.0 Hz, 1H), 2.79 (d, J=4.4 Hz, 3H).

EXAMPLE 10

Determination of antagonistic activity of cyclic N,N'-diarylthioureas and N,N'-diarylureas of the general formula 1 and their analog MDV3100 towards androgen receptors. The ability of novel cyclic N,N'-diarylthioureas and N,N'-diarylureas of the general formula 1 and MDV3100 agent to block androgen receptors was determined by their effectiveness of inhibition of dihydrotestosterone stimulated expression of prostate specific antigen (PSA) in cancer cells of human prostrate LNCap, derived from the American Tissue Culture Collection (ATCC, USA). These cells are sensitive towards 5-α-dihydrotestosterone (DHT) and in its presence produce cancer markers (PSA). The cells were cultured in RPMI 1640 medium (Invitrogen, USA) containing 10% calf serum (Hyclone, USA), 1% antibacterial/antifungal mixture (Sigma, USA) and 4,5% glucose. Before the experiment the cells were washed and suspended in the same medium in which, however, instead of calf serum the serum which had been treated with charcoal for removal of hormone traces was used. The cells were embedded into wells of 96-well plates by 100 μl per cell (10 000 cells) and left for 4 days in incubator at 37° C. (100% humidity) in atmosphere of 95% air/5% $CO_2$. After incubation cyclic N,N'-diarylthioureas or N,N'-diarylureas of the general formula 1 were added to the cells in various concentrations, and then—20 nM DHT (concentration corresponding to 80-90% of maximum stimulation). The cells were left for 5 days for additional incubation under the same conditions. After that the samples of supracellular medium were taken on analysis for PSA content. The test was carried out according to the protocol, recommended by manufacturer of the kit for determination of PSA (Alpha Diagnostic International, USA). After wetting the wells containing PSA antibodies attached to their bottom to each well 25 μl of the tested compounds and 100 μl of PSA antibodies conjugated previously with horseradish peroxidase were added successively.

After incubation at room temperature for 30 minutes, the contents of the wells were removed, the wells were washed several times, and then 100 μl of chromogenic substrate of peroxidase was added to each well. Plates were held for 15 min. at room temperature, after that 50 μl of stop solution was added to every well; at that a dye is formed the absorption intensity of which was measured at 450 nM; the value obtained is proportional to PSA concentration in the sample. Based on the dependence of lowering of PSA synthesis, caused by dihydrotestosterone (DHT), on the concentration of the tested compounds, dose-response curves were plotted, from which $IC_{50}$ values were determined. They were used for calculation of the values of apparent inhibition constants ($K_i$) for the compounds of the general formula I according to Cheng-Prusoff equation. [Cheng, Y., Prusoff, W. H. "Relationship between the inhibition constant ($K_i$) and the concentration of inhibitor which causes 50 percent inhibition ($IC_{50}$) of an enzymatic reaction". *Biochem Pharmacol.* (1973) 22, 3099-3108]:

$$K_i = IC_{50}/(1+L/K_D),$$

wherein L—agonist concentration (DHT), $K_D$—receptor activation constant, numerically equal to $EC_{50}$ value, which is determined in every experiment according to dependence of stimulation of PSA synthesis on DHT concentration.

The data obtained given in the corresponding examples testify that novel androgen receptor antagonists, in some cases, are more active than MDV3100, tested under the same conditions as a compound for comparison, for which $K_i^{MDV3100} = 79.5$ nM.

EXAMPLE 11

Determination of maximum tolerated dose of novel antagonists 1.2.3(1), and 1.2.3(3) and its analog MDV3100. Maximum tolerated dose (MTD) of novel antagonists 1.2.3 (1) and 1.2.3(3) and its analog MDV3100 were determined in experiments on male mice of CD1 line at peroral administration 1 time a day within 5 days in doses 10, 30 and 100 mg/kg. The compound was dissolved in sterile water with addition of Twin-80. Sterile water with Twin-80 was introduced to control animals (Placebo group). Body weight was appreciated, and also animals' mortality rate. Statistical comparison of groups was carried out according to non-parametric test ANOVA, with the use of Statistica programme.

At the administering compounds 1.2.3(1) or 1.2.3(3) in dose up to 100 mg/kg mice death was not observed. On the 3rd-4th day body weight of mice in the group, received the tested compound in dose 100 mg/kg was less in comparison with the body weight of control animals, however, statistical significance at this was not observed (FIG. 1). The data show that compound 1.2.3(1) and 1.2.3(3) has MTD >100 mg/kg.

At the administering MDV3100 in doses 10 and 30 mg/kg mice death was not observed. In the group of mice to which the tested compound was introduced in dose 100 mg/kg, the body weight began to lower on the $3^{rd}$ day. On the $5^{th}$ day body weight of this group of animals statistically differed from body weight of animals from Placebo group (p=0.002, FIG. 2). One animal died. The data show that compound MDV3100 has MTD ~30 mg/kg.).

EXAMPLE 12

The antitumor activity of (S)-1.2.3(1), a new androgen receptor antagonist, in the xenograft model of human breast cancer was studied. The suspension of human breast cancer cells MCF-7 was implanted subcutaneously into immunodeficient mice (1.0×107 cells in 0.2 ml of matrigel:medium 1:1). Estradiol benzoate was administered to mice subcutaneously (100 mg/mouse), 2 times a week. Upon reaching the mean tumor size of about 120 mm³ the mice were divided into groups (8 animals per group). After randomization the treatment started—the control group received solvent (0.5% methyl cellulose solution), the experimental group received (S)-1.2.3(1) in dosage of 20 mg/kg—one and two times a day, depending on the group. The treatment was carried out at intragastric administration, the volume—5 ml/kg.

During the study the size of tumors in animals and the weight of the animals were measured 2 times a week as well as toxicity symtoms. Based on the results the tumor growth inhibition were calculated T/C (experiment/control*100%).

Tumor volume (mm³): Length×width²×0.5, mm³.

Tumor growth inhibition (T/C) was calculated by formula:

$$T/C = (T_n - T_1/C_n - C_1) \times 100\%;$$

If $(T_n - T_1) < 0$, then $T/C = (T_n - T_1)/T_1 \times 100\%;$ $C_1$ (Cn): tumor volume in the day 1 (or day n) in the group of control;

$T_1$ (Tn): tumor volume in the day 1 (or day n) in the group of experiment.

The value T/C≤42% was considered as efficiency of antitumor activity.

The samples of blood plasma and tumor were collected and frozen at the end of the study to determine the concentration of the substance. There were no symptoms of toxicity during intragastric administration of (S)-1.2.3(1). FIG. 3 shows the weight of animals. It can be seen that there were any symptoms of weight loss during the treating of (S)-1.2.3(1) at a dosage of 20 mg/kg neither in the treatment once a day, nor in the treatment twice a day.

FIG. 4 shows the curves of tumor growth in animals in the control and experimental groups. It can be seen that the treating animals of (S)-1.2.3(1) at a dosage of 20 mg/kg resulted in high tumor growth inhibition of human breast cancer. The effect began after 13 days of treatment and gradually increased. The most high inhibition of tumor growth in the experimental groups was on days 5, 25 and 33 (for the treatment once a day) and on days 25 and 35 (for the treatment 2 times a day).

(S)-1.2.3(1) shows a high tumor growth inhibition of breast cancer in both treatment regimens.

EXAMPLE 13

Preparation of medicament in the form of tablets. Starch (1600 mg), grained lactose (1600 mg), talcum (400 mg) and N-methyl-4-{4-oxo-2-thioxo-3-[3-(trifluoromethyl)-4-cyanophenyl]-7-oxa-1,3-diazaspiro[4.4]non-1-yl}-2-fluorobenzamide 1.2.3(1) (1000 mg) mixed together and pressed in a brick. Prepared brick was crushed to granules and riddled through sieves, gathering granules of 14-16 mesh size. The obtained granules were pelletised in tablets of suitable form of 560 mg by weight each.

EXAMPLE 14

Preparation of medicament in the form of capsules. The compound 1.2.3(1) was carefully mixed with lactose powder in ratio 2:1. The prepared pharmaceutical composition was packed on 300 mg into gelatinous capsules of suitable size.

EXAMPLE 15

Preparation of medicament in the form of composition for intramuscular, intraperitoneal or hypodermic injections. The compound 1.2.3(1) (500 mg) was dissolved in the mixture of chlorobutanole (300 mg), propylene glycol (2 ml), and water for injections (100 ml). The prepared solution was filtered and placed in 1 ml ampoules which were sealed up and sterilized in an autoclave.

INDUSTRIAL APPLICABILITY

The present invention could be used in medicine, veterinary, biochemistry.

The invention claimed is:

1. A pharmaceutical composition comprising a pharmaceutically effective amount of a 4-[3-(4-cyano-3-trifluoromethyl-phenyl)-4-oxo-2-thioxo-7-oxa-1,3-diaza-spiro[4.4]non-1-yl]-2-fluoro-benzimide compound of general formula 1 or an (R)-enantiomer thereof and a pharmaceutically acceptable carrier or an excipient

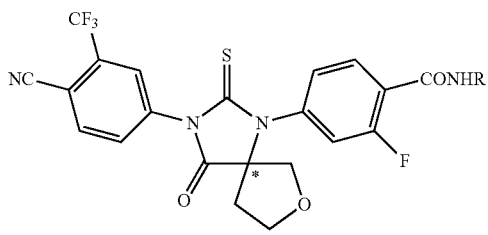

1 wherein:
R is $C_1$-$C_3$alkyl.

2. A pharmaceutical composition according to claim 1, wherein the compound is 4-[(R)-3-(4-cyano-3-trifluoromethyl-phenyl)-4-oxo-2-thioxo-7-oxa-1,3-diaza-spiro[4.4]non-1-yl]-2-fluoro-benzimide represented by formula (R)-1

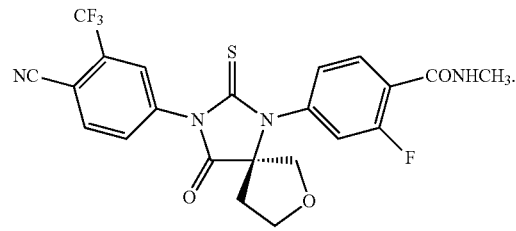

(R)-1

3. The composition according to claim 1 in the form of a capsule.

4. The composition according to claim 1 in the form of a tablet.

5. The composition according to claim 1 in the form of an injection.

* * * * *